United States Patent
Gerber et al.

Patent Number: 5,836,928
Date of Patent: Nov. 17, 1998

[54] SPINAL FLUID COLLECTION SYSTEM

[76] Inventors: Allen Gerber, 42 Nutmeg Rd., Highfalls, N.Y. 12440; Lewis Gluck, 14 Fox Run, Wappingers Falls, N.Y. 12590; John G. Costa, P.O. Box 278, Highland, N.Y. 12528

[21] Appl. No.: 795,342

[22] Filed: Feb. 4, 1997

[51] Int. Cl.$^6$ .............................. A61B 5/00; A61M 1/00
[52] U.S. Cl. ..................... 604/317; 600/576; 600/577; 600/578; 600/583
[58] Field of Search ................................. 604/317, 403, 604/411, 412, 414; 600/576, 577, 578, 573, 583

[56] References Cited

U.S. PATENT DOCUMENTS

| | | | |
|---|---|---|---|
| 2,138,988 | 12/1938 | Thomas. | |
| 3,920,002 | 11/1975 | Dye et al. | 128/760 |
| 3,978,846 | 9/1976 | Bailey | 128/760 |
| 5,078,688 | 1/1992 | Lobodzinski et al. | 604/317 |
| 5,195,534 | 3/1993 | Sarrine | 128/764 |
| 5,207,661 | 5/1993 | Repschlager | 604/317 |
| 5,251,786 | 10/1993 | Sarrine | 222/206 |
| 5,396,899 | 3/1995 | Strittmatter | 604/403 |

*Primary Examiner*—Robert A. Clarke
*Assistant Examiner*—David J. Cho
*Attorney, Agent, or Firm*—John G. Costa

[57] ABSTRACT

A Spinal Fluid Collection System comprising means to prevent complete withdrawal of a needle stylet, means to dispose of needles and needle stylets and means to collect fluid samples provides for limited exposure to spinal fluid samples and to needle sticks from spinal tap needles and stylets during and after the performance of a spinal tap.

6 Claims, 3 Drawing Sheets

SPINAL FLUID COLLECTION SYSTEM

FIELD OF THE INVENTION

The present invention relates to an improved system for collecting spinal fluid samples.

BACKGROUND OF THE INVENTION

The need for protection from exposure to needle sticks has been the impetus to the development of needle guards and needle protectors. Furthermore, an increased awareness of transmission of infections from exposure to body fluids or other samples has led to the development of improved means to limit exposure to samples collected. An example of both a risk of sustaining a needle stick and also exposure to collected samples is the current procedure for the drawing of spinal fluid during a spinal tap. Typically, a needle with a stylet is inserted between the appropriate vertebrae, the stylet is removed and multiple vials are handled during the procedure. There is risk of breakage and leakage and consequent exposure of personnel to the samples collected. Also, when the needle or stylet is withdrawn during and after the procedure, there is risk of being stuck by either the needle or the stylet.

A number of systems have been devised to protect individuals from needle sticks while using syringes and angiocatheters. However, users of needles for other purposes, such as spinal taps, still have no protective devices suitable for their needs.

In U.S. Pat. No. 5,396,899, Strittmatter disclosed an apparatus to limit leakage when spinal fluid is collected.

It is an object of the present invention to provide means for limiting exposure to needle sticks from spinal tap needles during and after the performance of a spinal tap.

It is another object of the present invention to provide means for limiting exposure to sticks from spinal tap stylets during and after the performance of a spinal tap.

It is a further object of the present invention to provide means for limiting exposure to spinal fluid samples during and after the performance of a spinal tap.

DETAILED DESCRIPTION OF THE PREFERRED EMBODIMENT

The system is fully understood by referring to a description of the figures.

Figure 1:
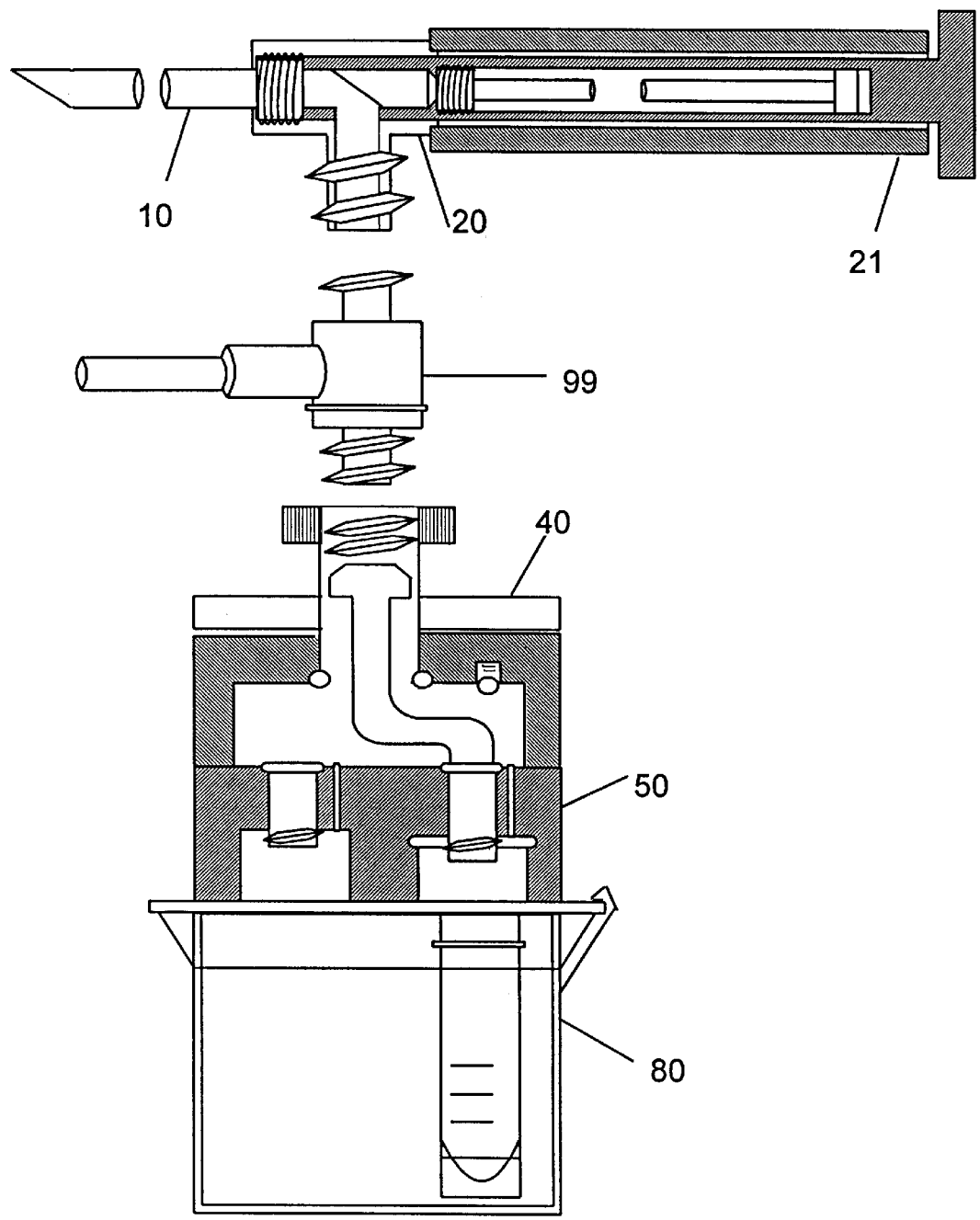
FIG. 1 is a cross-sectional view of the system of the invention.

FIG. 1 is a cross-sectional view of the system of the invention.

Referring to FIG. 1, the system comprises needle unit 10, guide 20, disposal unit 21, transmission means 40, container holding means 50, optional cover 80, and optional adapter 99. The hub of the needle unit is positioned within the guide. The guide and the hub are attached to the disposal unit. The guide is attachable either directly or indirectly to the transmission means. The transmission means and the container holding means function together as a unit. An optional cover is latched onto the container holding means and provides further protection in the event of breakage or leakage of one of the enclosed containers. Preferably, the parts of the system, especially the guide and the hub, are transparent to enable viewing of the flow of spinal fluid during the spinal tap procedure.

When the system is used as described, any spinal fluid collected will remain enclosed within the system and exposure to needle stick or spinal fluid will be minimized.

Prior to performing a spinal tap, the user configures the system for his or her convenience. If the needle unit is not already positioned within the guide, the needle unit is inserted within the guide. If the disposal unit is attached to the guide and to the hub of the needle unit, the disposal unit is detached. If sample collection containers have not already been inserted into the container holding means or if different containers are desired by the user, the appropriate changes are made. Preferably, a cover is applied. And, the attachment of the guide to the transmission unit is configured as desired by the user. In the preferred embodiment, once the configuration is complete, the system is completely enclosed.

In the performance of a spinal tap, utilizing sterile technique, the user inserts the spinal needle into the subarachnoid space. The needle stylet is withdrawn and spinal fluid flows into the hub of the needle. The spinal fluid then flows from the hub, through a port in the guide and then either directly or through one or more adapters to the transmission means. In the embodiment depicted in FIG. 1, a flexible tube, not shown, conveys fluid from the guide to the adapter shown. The adapter is attached either directly or indirectly to the transmission means and spinal fluid flows through the adapter to the transmission means. Adapters are used for the convenience and preference of the individual user. However, the guide can be directly attached to the transmission means.

The transmission means and the container holding means function as a unit. These means are movable relative to each other. Movement of the transmission means relative to the container holding means or of the container holding means relative to the transmission means permits the sequential filling of sample containers held in the container holding means. Said movement may be circular, linear or any other displacement of the transmission means and the container holding means relative to each other which permits the sequential filling of sample containers held in the container holding means.

In the embodiment depicted in FIG. 1, the transmission means is rotatable relative to the container holding means. The container holding means holds one or more sample collection containers. Rotation of the transmission means of FIG. 1 enables the sequential filling of the sample collection containers held in the container holding means. When the desired amount of fluid has been collected in a given container, the transmission means is rotated and the next container is filled to the desired level. When the desired number of containers have been filled to their desired levels, the stylet is reinserted into the needle and the spinal needle is removed from the subarachnoid space.

Once the spinal tap procedure is completed, the disposal unit is attached to the guide and to the hub of the needle unit.

The needle unit, including the stylet, is withdrawn into the disposal unit and the entire system is sent to the laboratory where the samples collected are removed for analysis and the system is disposed of under controlled conditions.

Figure 2A:
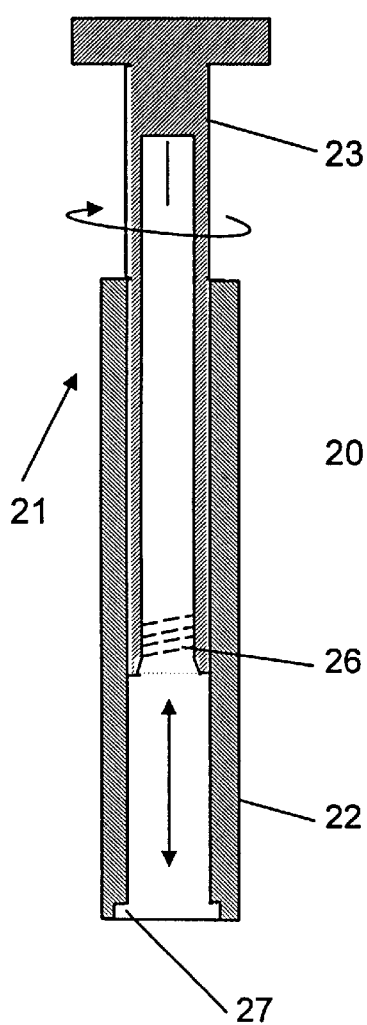
FIG. 2a is a detailed cross-sectional view of a needle unit of the invention.
Figure 2B:
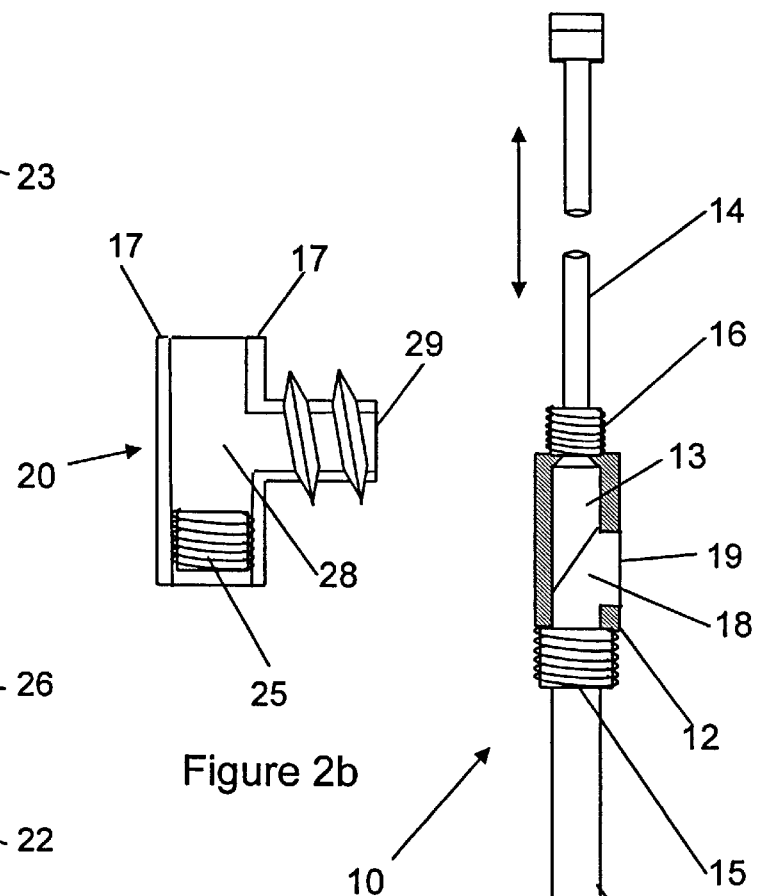
FIG. 2b is a detailed cross-sectional view of a guide of the invention.
Figure 2C:
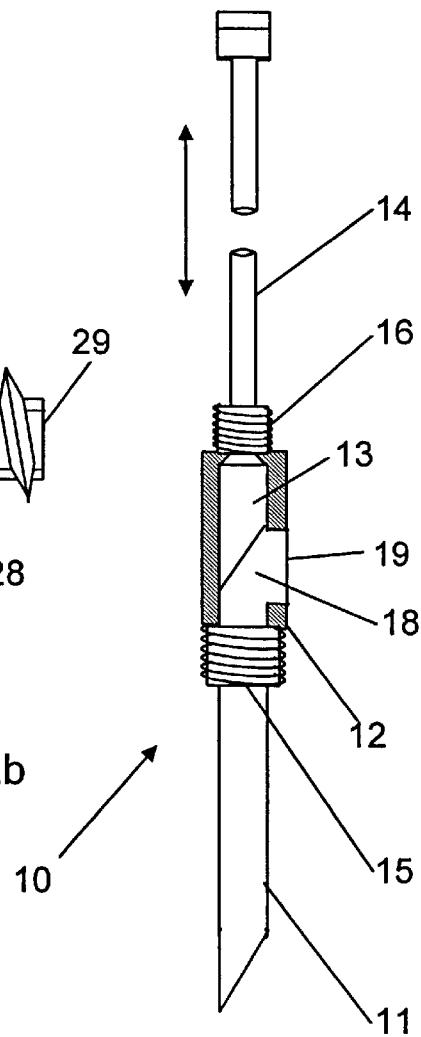
FIG. 2c is a detailed cross-sectional view of a disposal unit of the invention.

In FIGS. 2a, 2b, and 2c, the complementary relationship of needle unit 10, guide 20, and disposal unit 21 are illustrated.

The system uses a number of complementary engagement means. Complementary engagement means can be used, but are not required on transmitting and receiving ports. Transmitting and receiving ports are adapted to each other, using complementary engagement means or otherwise, such as by means of conventional seals, in order to limit leakage and to direct flow. Complementary engagement means are also used to maintain or establish an attachment of one part of the system to another part of the system. Specific complementary engagement means are illustrated and described for convenience of explanation. However, the complementary parts of any suitable fastener may be used as complementary engagement means in place of those illustrated and described. One example of complementary engagement means is an internal thread and an external thread. Another example of complementary engagement means is a snap comprising a hole and a projection, such as, for example, a plug or ball, which fits snugly into said hole. Thus, when an external thread is employed as the engagement means of the hub, an internal thread is employed as the engagement means of the disposal unit; or when an external thread is employed as the engagement means of the disposal unit, an internal thread is employed as the engagement means of the hub. Furthermore, instead of using a set of threads as the complementary engagement means of the hub and the disposal unit, another type of complementary engagement means, such as, for example, a snap can be used.

Referring to FIGS. 2a, 2b and 2c, needle unit 10 comprises hollow needle 11, hub 12 and a needle stylet.

Preferably, needle 11 is permanently attached to hub 12 at the distal end of the hub. The hub comprises engagement means 15 at the distal end of the hub, engagement means 16 at the proximal end of said hub, chamber 18, and port 19. Port 19 communicates directly with chamber 18. When the stylet is removed from the lumen of the needle, spinal fluid flows through the lumen and an aperture at the distal end of the hub into chamber 18 of the hub. An aperture at the proximal end of the hub permits the slidable displacement of the stylus within the hub and the needle. The distal end of the stylus is wider than the aperture at the proximal end of the hub. The distal end 13 of the stylet is broader than the shaft 14 of the stylet. Preferably, the stylet is tapered from the distal end 13 to the shaft 14. Only the distal end of the stylet enters the subarachnoid space during a spinal tap procedure. During the performance of a spinal tap the stylet is withdrawn through the aperture at the proximal end of the hub. The cross-sectional dimensions of the aperture at the proximal end of the hub permit passage of the shaft of the stylet and prevent passage of the distal end of the stylet. Upon optimal withdrawal of the stylet, the distal end of the stylet remains within the hub but does not occlude the flow of spinal fluid through any port in the hub. That is, optimal withdrawal of the stylet permits unobstructed flow through any port in the hub. The shaft of the stylet fits snugly in the aperture at the proximal end of the hub to limit any leakage of spinal fluid. Since only the shaft is small enough to pass through the aperture at the proximal end of the needle hub, upon maximum withdrawal of the stylet from the needle, the end of the stylet which had entered the subarachnoid space remains within the needle hub.

Guide 20 comprises engagement means 25 at the distal end of the guide, engagement means 17 at the proximal end of the guide, chamber 28, and port 29. Engagement means 25 is complementary to engagement means 15. Hub 12 is securely positioned within guide 20 by the engagement of engagement means 15 and engagement means 25. In the illustration of FIG. 2, engagement means 15 and engagement means 25 are threads. However, any suitable complementary means can be substituted for these threads. Port 29 of guide 20 is aligned with port 19 of hub 12 so that spinal fluid in chamber 18 of the hub flows through port 19 and then through port 29.

Disposal unit 21 comprises rigid cylinder 22 and plunger 23. Rigid cylinder 22 comprises engagement means 27 at the distal end of the rigid cylinder and plunger 23 comprises engagement means 26 at the distal end of the plunger. Engagement means 27 is complementary to engagement means 17. Rigid cylinder 22 securely attaches to guide 20 by the engagement of engagement means 17 and engagement means 27. Engagement means 17 and engagement means 27 are any suitable complementary engagement means such as, for example, threads. At the end of the spinal tap procedure, the user engages engagement means 27 and engagement means 17 to securely hold and stabilize guide 20. Then the user engages engagement means 26 and engagement means 16. Engagement means 26 is complementary to engagement means 16. Preferably, the engagement of engagement means 27 and engagement means 17 prevents the rotation of guide 20. Hub 12 is removed from within guide 20 by the engagement of engagement means 16 and engagement means 26 and the simultaneous disengagement of engagement means 15 and engagement means 25. In the illustration of FIG. 2, engagement means 16 and engagement means 26 are threads. However, any suitable complementary means can be substituted for these threads. In the embodiment illustrated, the threading of complementary engagement means 15 and 25 are the reverse of the threading of complementary engagement means 16 and 26 so that a turning of plunger 23 to engage engagement means 16 and 26 simultaneously disengages engagement means 15 and 25. Once engagement means 15 are disengaged from engagement means 25, the user can turn or pull plunger 23 to withdraw the needle unit into the disposal unit.

In FIGS. 2a,2b, and 2c,plunger 23 is internally threaded to engage the externally threaded distal end of hub 12. If the entire length of the internally threaded plunger 23 is threaded and the external threads of the distal end of the hub are of suitable diameter, for example, greater than the diameter of the remainder of said hub, when the hub is engaged by the plunger, a turning of the plunger withdraws the needle unit into the disposal unit.

If only a segment of plunger 23 is internally threaded to engage the externally threaded distal end of hub 12, when the hub is engaged by the plunger, a pulling of the plunger withdraws the needle unit into the disposal unit.

Figure 3A:
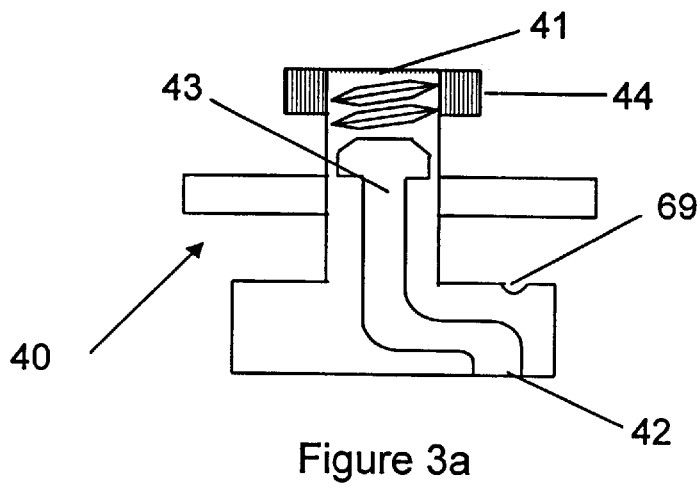
FIG. 3a is an exploded cross-sectional view of the transmission means of the invention.
Figure 3B:
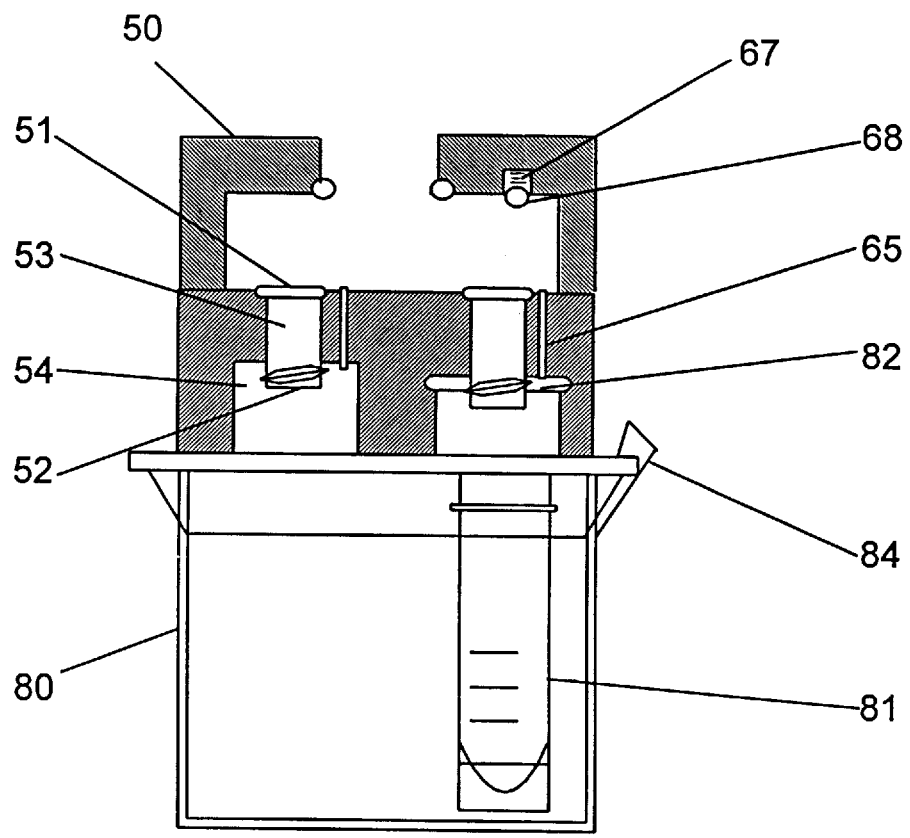
FIG. 3b is an exploded cross-sectional view of the container holding means of the invention.

FIGS. 3a and 3b depicts detailed cross sections of transmission means 40 and container holding means 50. Cover 80 is reversibly attached to the container holding means by latch 84.

The transmission means comprises a channel to transmit fluid from a needle unit to a container holding means. Either a needle unit or a guide is adapted to engage the transmission means either directly or by means of one or more adapters. The transmision unit is also adapted to engage a sample container, either directly or by means of one or more adapters. Thus, the transmission unit is adapted to receive fluid from the needle unit and to transmit fluid from the needle unit to the container. For example, as illustrated in FIGS. 3a and 3b, transmission means 40 comprises external port 41, channel 43 and internal port 42. External port 41 is adapted to engage port 29 of guide 20, or the port of an adapter such as adapter 99. That is, external port 41 and port 29 are complementary engagement means. Spinal fluid received either directly or indirectly from port 29 at external port 41 then flows through channel 43 to internal port 42.

Container holding means 50 comprises at least one adapter 53, and at least one container holding recess 54. Adapter 53 comprises an external port 51 and an internal port 52. Sample container 81 comprises an optional cap 82. Each sample container comprises a port which is adapted to engage internal port 52 of adapter 53. In the embodiment illustrated, cap 82 comprises the port adapted to engage internal port 52 of adapter 53. In operation, a container 81 is positioned in one or more container holding recesses 54. Adapter 53 is adapted at external port 51 to receive spinal fluid from internal port 42 of transmission means 40 and adapted at internal port 52 to transmit said spinal fluid to the port of a sample container or a sample container cap. That is, external port 51 and internal port 42 are complementary engagement means and internal port 52 and the port of the sample container are complementary engagement means.

The transmission means and the container holding means are movable relative to each other. In the embodiment illustrated, said movement is a circular rotation. The transmission means preferably comprises an internally threaded engagement means 44 adapted to engage the external threads of port 29 or the external threads of a port of an adapter such as adapter 99. Engagement means 44 is rotatably attached to the transmission means. When engagement means 44 engages the external threads of port 29 or the external threads of a port of an adapter such as adapter 99, port 41 is securely but rotatably engaged to port 29 or an externally threaded port of an adapter such as adapter 99 and port 41 is freely rotatable relative to port 29. Preferably, engagement means 29 and engagement means 41 are seals, such as, for example, O-rings, which are sealably pressed together when engagement means 44 engages the external threads of port 29.

In the embodiment illustrated in FIGS. 3a and 3b, spinal fluid flows from external port 41 through channel 43 to internal port 42. Flow continues through port 42, into port 51, through adapter 53 to port 52. From port 52 flow then goes through a port in cap 82 into container 81. Once the desired quantity of fluid is collected in a sample container, the transmission means is rotated until port 52 engages a port in another cap 82. Preferably, the interface between the transmission means and the top of the containers is a seal, such as an O-ring, which prevents leakage from filled containers. Thus, once a container is filled to the desired level, the rotation of the transmission means to enable the filling of the next container in sequence, also seals the tops of containers which have already been filled.

Preferably, in order to prevent leakage, an O-ring or other seal is placed between the transmission means and the container holding means, between ports 29 and 41, between ports 42 and 51, between port 52 a port in cap 82, and in any other part of the system where leakage might occur. The seal between the transmission means and the container holding means is utilized to prevent leakage from sample containers. Also, it is preferred to include an index means in the system which will stop rotation of the transmission means when port 52 engages and is aligned with a port in another cap 82. Any suitable index means can be used. For example, the index means illustrated comprises ball 68, spring 67, and hemispherical indent 69. During rotation of transmission means 40, whenever ball 68 engages a hemispherical indent 69, the tension of spring 67 forces ball 68 into a hemispherical indent 69 and stops said rotation. A slight force is applied by the operator to overcome the resistance of the spring so that the transmission means can be rotated to the next desired position. It is preferred that a brake be provided after the filling of the last sample container. Said brake functions in the same manner as the index means and can utilize the same ball and spring with the replacement of the hemispherical indent with a deeper indent. When the ball falls into said deeper indent, further rotation of the transmission means is prevented. There is one hemispherical indent 69 or a brake for each recess 54. It is also preferred that air vents 65 be provided where needed to enable release of air through caps 82 during the filling of containers 81.

The foregoing description and accompanying drawings are provided for illustration and example. It is understood that various changes, adaptations and modifications may be made without departing from the spirit of the invention which is limited only by the scope of the claims which follow.

What is claimed is:

1. A spinal fluid collection system comprising a needle unit, a guide, a disposal unit, transmission means and container holding means; said needle unit comprising a hub; said disposal unit comprising a rigid cylinder and a plunger; said guide comprising engagement means complementary to engagement means of said hub wherein the engagement of the complementary engagement means of said guide and said hub attaches said guide to said hub; said guide comprising engagement means complementary to engagement means of said rigid cylinder wherein the engagement of the complementary engagement means of said guide and said rigid cylinder attaches said guide to said rigid cylinder; said plunger comprising engagement means complementary to engagement means of said hub wherein the engagement of the complementary engagement means of said plunger and said hub attaches said plunger to said hub and permits the withdrawal of said hub into said rigid cylinder; said hub comprising a chamber and a port, wherein the port of said hub receives fluid from said chamber and transmits said fluid to a port of said guide; said guide comprising a port, wherein the port of said guide is adapted to transmit said fluid received from the port of said hub to said transmission means; said transmission means comprising a channel external port, a channel, and a channel internal port, wherein said channel transmits fluid received at said channel external port to said channel internal port, said channel external port is adapted to receive fluid from said guide, and said channel internal port is adapted to transmit fluid to one or more sample containers; said container holding means comprising at least one adapter and at least one container holding recess, each said adapter comprising an adapter external port and an adapter internal port, each adapter external port adapted to receive fluid from said transmission means, each adapter internal port adapted to transmit fluid to a specimen container positioned in said container holding recess.

2. The system of claim 1, said needle unit further comprising a stylet, wherein the distal end of said stylet is wider than the shaft of said stylet and wherein said hub further comprises an aperature at the proximal end of said hub, said aperature permitting the passage of the shaft of said stylet and preventing the passage of the distal end of said stylet.

3. The system of claim 2 wherein optimal withdrawal of said stylet permits unobstructed flow through the port of said hub.

4. The system of claim 1 wherein said transmission means and said container holding means are movable relative to each other to permit the sequential filling of sample containers held in the container holding means.

5. The system of claim 4 wherein movement of the transmission means and the container holding means relative to each other is circular.

6. The system of claim 4 wherein movement of the transmission means and the container holding means relative to each other is linear.

* * * * *